(12) United States Patent
Wang et al.

(10) Patent No.: US 12,257,085 B2
(45) Date of Patent: Mar. 25, 2025

(54) CT SCANNING METHOD AND SYSTEM, ELECTRONIC DEVICE, AND COMPUTER-READABLE STORAGE MEDIUM

(71) Applicants: BEIJING FRIENDSHIP HOSPITAL, CAPITAL MEDICAL UNIVERSITY, Beijing (CN); TSINGHUA UNIVERSITY, Beijing (CN)

(72) Inventors: Zhenchang Wang, Beijing (CN); Li Zhang, Beijing (CN); Hongxia Yin, Beijing (CN); Yuxiang Xing, Beijing (CN); Zhiqiang Chen, Beijing (CN); Kejun Kang, Beijing (CN); Liang Li, Beijing (CN); Pengfei Zhao, Beijing (CN); Zhengyu Zhang, Beijing (CN); Jing Li, Beijing (CN); Han Lv, Beijing (CN)

(73) Assignees: BEIJING FRIENDSHIP HOSPITAL, CAPITAL MEDICAL UNIVERSITY, Beijing (CN); TSINGHUA UNIVERSITY, Beijing (CN)

( * ) Notice: Subject to any disclaimer, the term of this patent is extended or adjusted under 35 U.S.C. 154(b) by 281 days.

(21) Appl. No.: 18/085,522

(22) Filed: Dec. 20, 2022

(65) Prior Publication Data
US 2023/0190210 A1 Jun. 22, 2023

(30) Foreign Application Priority Data
Dec. 21, 2021 (CN) .......................... 202111572451.9

(51) Int. Cl.
*A61B 6/00* (2024.01)
*A61B 6/03* (2006.01)
(Continued)

(52) U.S. Cl.
CPC ............ *A61B 6/032* (2013.01); *A61B 6/0407* (2013.01); *A61B 6/542* (2013.01); *A61B 6/583* (2013.01);
(Continued)

(58) Field of Classification Search
None
See application file for complete search history.

(56) References Cited

U.S. PATENT DOCUMENTS

2009/0060121 A1   3/2009   Ziegler et al.
2009/0285357 A1   11/2009  Khamene et al.
(Continued)

FOREIGN PATENT DOCUMENTS

CN   101405619 A    4/2009
CN   104224212 A   12/2014
(Continued)

OTHER PUBLICATIONS

CN Office Action in application No. 202111572451.9 dated Oct. 24, 2022.
(Continued)

*Primary Examiner* — Hoon K Song
(74) *Attorney, Agent, or Firm* — Maschoff Brennan

(57) ABSTRACT

Provided are a CT scanning method and system, an electronic device, and a computer-readable storage medium. The method includes: determining a first coordinate of a mark point of a part to be imaged in a dual-camera coordinate system; converting the first coordinate into a second coordinate of the mark point in a CT coordinate system according to coordinate system transformation parameters; generating first locating information according to the second coordinate to drive a scanning table to move to a first location designated by the first locating information; obtaining projection images of the part to be scanned; determining
(Continued)

second locating information and scanning information of the part to be scanned according to the projection images; and driving the scanning table to move to a second location designated by the second locating information according to the second locating information and performing CT scanning according to the scanning information.

20 Claims, 3 Drawing Sheets

(51) Int. Cl.
    *A61B 6/04*          (2006.01)
    *A61B 6/58*          (2024.01)
    *G06T 7/00*          (2017.01)
    *G06V 10/82*        (2022.01)

(52) U.S. Cl.
    CPC ............ *G06T 7/0012* (2013.01); *G06V 10/82* (2022.01); *G06T 2207/10081* (2013.01); *G06T 2207/20081* (2013.01)

(56) References Cited

U.S. PATENT DOCUMENTS

| | | | | |
|---|---|---|---|---|
| 2009/0296893 | A1* | 12/2009 | Strobel | A61B 6/032 378/207 |
| 2010/0215142 | A1 | 8/2010 | Dafni et al. | |
| 2010/0215149 | A1* | 8/2010 | Takemoto | A61B 17/12113 378/98 |
| 2015/0086101 | A1 | 3/2015 | Bhagalia et al. | |
| 2015/0238159 | A1* | 8/2015 | Al Assad | A61B 6/4014 378/5 |
| 2016/0183905 | A1 | 6/2016 | Lou et al. | |
| 2018/0098744 | A1* | 4/2018 | Bauer | A61B 6/4014 |
| 2019/0076101 | A1 | 3/2019 | Pan et al. | |
| 2021/0330272 | A1 | 10/2021 | Xiong et al. | |

FOREIGN PATENT DOCUMENTS

| | | |
|---|---|---|
| CN | 104352246 A | 2/2015 |
| CN | 106510747 A | 3/2017 |
| CN | 112258593 A | 1/2021 |
| CN | 112700499 A | 4/2021 |
| CN | 113180709 A | 7/2021 |
| CN | 113538707 A | 10/2021 |
| CN | 113674205 A | 11/2021 |
| EP | 3 905 130 A1 | 11/2021 |
| WO | 2023/272372 A1 | 1/2023 |

OTHER PUBLICATIONS

CN Office action in application No. 202111572451.9 mailed Jan. 5, 2023.
CN Office action in application No. 202111572451.9 mailed Mar. 24, 2023.
EESR in EP application 22214977.5 issued May 23, 2023.
CA Office Action dated May 15, 2024 as received in Application No. 3184370.

* cited by examiner

CT SCANNING METHOD AND SYSTEM, ELECTRONIC DEVICE, AND COMPUTER-READABLE STORAGE MEDIUM

TECHNICAL FIELD

The present disclosure relates to the technical field of medical devices, and in particular to a CT scanning method and system, an electronic device, and a computer-readable storage medium.

BACKGROUND

In the medical field, CT has been widely used as a basic inspection method. However, at present, limited by its spatial resolution, a traditional CT cannot meet a diagnostic requirement in terms of imaging fine body structures such as the temporal bone, so doctors are unable to use a traditional CT as an inspection method when diagnosing minimal hidden lesions, thus affecting the efficacy of CT in clinical applications.

In the process of image acquisition, the traditional CT usually adopts manual positioning and locating of scanning regions, etc. Such modes are not only inefficient in operation but also cause the following problems in practice due to a large individual differences of patients: (1) if a scanning region is larger than necessary, a radiation dose to a patient can be large to cause unnecessary negative influence to the patient; and (2) if the scanning region is too small or deviated, the targeted region of interest (ROI) cannot be completely covered, so that re-scanning is required, thereby causing additional radiation injury to the patient.

SUMMARY

Embodiments of the present disclosure provide a CT scanning method and system, an electronic device, and a computer-readable storage medium, so as to solve the problems of low operation efficiency and unsatisfying scanning results of CT in the prior art caused by manual positioning and locating of a targeted region to scan.

In order to achieve the above purpose, an embodiment of the present disclosure provides a CT scanning method, including:
  determining, by dual-camera imaging of a part to be scanned, a first coordinate of a mark point of the part to be imaged by a dual-camera imaging system;
  converting the first coordinate into a second coordinate of the mark point in a CT coordinate system according to coordinate system transformation parameters;
  generating first locating information according to the second coordinate to drive a scanning table to move to a first location designated by the first locating information;
  obtaining projection images of the part to be scanned, wherein the projection images includes a front-back direction projection image and a side-side direction projection image for the part to be scanned;
  determining second locating information and scanning information of the part to be scanned according to the projection images, wherein the scanning information includes scanning region information and exposure parameter information; and
  driving the scanning table to move to a second location designated by the second locating information and performing CT scanning according to the scanning information.

Embodiments of the present disclosure also provide a CT scanning system, including: a positioning module and a scanning module.

The positioning module is configured to determine, by dual-camera imaging a part to be scanned, a first coordinate of a mark point of the part to be imaged in a dual-camera coordinate system, convert the first coordinate into a second coordinate of the mark point in a CT coordinate system according to coordinate system transformation parameters, and generate first locating information according to the second coordinate to drive a scanning table to move to a first location designated by the first locating information.

The scanning module is configured to obtain projection images of the part to be scanned, wherein the projection images includes a front-back direction projection image and a side-side direction projection image for the part to be scanned; determine second locating information and scanning information of the part to be scanned according to the projection images, wherein the scanning information includes scanning region information and exposure parameter information; and drive the scanning table to move to a second location designated by the second locating information and perform CT scanning according to the scanning parameters.

Embodiments of the present disclosure also provide a reconstruction algorithm using both full-view and detailed-view data, including:
  obtaining full-view scanning projection data and detailed-view scanning projection data;
  calculating conventional-resolution data of a region beyond the part to be scanned according to the full-view scanning projection data; and
  calculating detailed-view image data based on a conventional resolution beyond the region and the detailed-view scanning projection data; or
  obtaining full-view scanning grid pixel data and detailed-view scanning grid pixel data;
  respectively calculating full-view projection data of a region beyond the part to be scanned and detailed-view high-resolution projection data for the part to be scanned according to the full-view scanning grid pixel data and the detailed-view scanning grid pixel data; and
  calculating CT scanning image data by using an iterative algorithm based on the full-view projection data and the detailed-view high-resolution projection data.

Embodiments of the present disclosure also provide an electronic device, including:
  a memory, configured to store a program; and
  a processor, configured to execute the program stored in the memory, wherein the program, when executed, performs the CT scanning method provided by the embodiments of the present disclosure.

Embodiments of the present disclosure also provide a computer-readable storage medium, storing a computer program executable by a processor, wherein the program, when executed by the processor, implements the CT scanning method as provided by the embodiments of the present disclosure.

In the CT scanning method and system, the electronic device, and the computer-readable storage medium provided by the embodiments of the present disclosure, according to dual-camera imaging of a part to be scanned, a first coordinate of a mark point of the part to be imaged in a dual-camera coordinate system is determined. The first coordinate is converted into a second coordinate in a CT coordinate system according to coordinate system transformation parameters. Thus, first locating information is generated according to the second coordinate to drive a scanning table to move to a first location designated by the first locating information. Then, projection images of the part to be scanned are obtained. Second locating information and scanning information of the part to be scanned are determined according to the projection images. The scanning table is driven to move to a second location designated by the second locating information according to the second locating information and CT scanning is performed according to the scanning information. Thus, it is possible to determine a first location of a full-view scanning region according to the dual-camera images and a second location of a detailed-view scanning region according to the projection images as well as parameters for detailed-view scanning, whereby a target with a fine structure can be automatically positioned and accurately imaged through combining a full-view and detailed-view scan, and the defects of manual positioning and poor scanning effects in the prior art can be eliminated.

The above description is merely a summary of the technical solutions of the present disclosure. In order to more clearly know the technical means of the present disclosure to enable the implementation according to the contents of the description, and in order to make the above and other purposes, features and advantages of the present disclosure more apparent and understandable, specific implementations of the present disclosure are provided below.

BRIEF DESCRIPTION OF THE DRAWINGS

Various other advantages and benefits will become apparent to those ordinarily skilled in the art upon reading the following detailed description of the preferred implementations. The drawings are only for purposes of illustrating the preferred implementations and are not to be construed as limiting the present disclosure. Also throughout the drawings, the same reference numerals represent the same components. In the drawings.

DETAILED DESCRIPTION OF EXAMPLE EMBODIMENTS

Exemplary embodiments of the present disclosure will be described in more detail below with reference to the accompanying drawings. While the drawings show exemplary embodiments of the present disclosure, it should be understood that the present disclosure may be embodied in various forms and should not be limited by the embodiments set forth herein. Rather, these embodiments are provided so that the present disclosure will be thoroughly understood, and the scope of the present disclosure will be fully conveyed to those skilled in the art.

Embodiment 1

Figure 1:
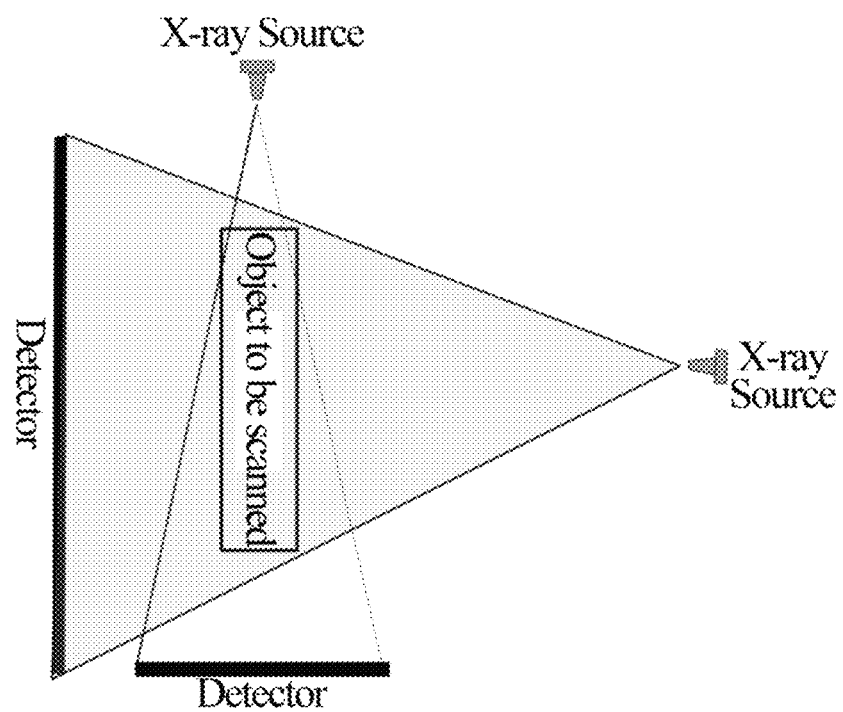
FIG. 1 is a schematic diagram of an application scenario of a CT scanning scheme according to an embodiment of the present disclosure.

A scheme provided by the embodiment of the present disclosure is applicable to any system having CT scanning capability, such as a CT scanning system. FIG. 1 is a schematic diagram of an application scenario of a CT scanning scheme according to an embodiment of the present disclosure. A scenario shown in FIG. 1 is merely one example of a scenario to which the technical solution of the present disclosure can be applied.

In the medical field, CT has been widely used as a basic examination means. However, limited by its spatial resolving power, the current CT cannot meet the requirements of diagnosis in the imaging of the temporal bone and other fine human structures. Thus, doctors cannot use CT as an examination means in the diagnosis of small occult lesions, thereby affecting the effectiveness of CT in clinical application.

In the process of image acquisition, the traditional CT usually adopts manual positioning and locating of scanning regions, etc. Such modes not only are inefficient in operation but also cause the following problems in practice due to large individual differences of patients: (1) if a scanning region is larger than necessary, a radiation dose to a patient can be large to cause unnecessary negative influence to the patient; and (2) if the scanning region is too small or deviated, the targeted ROI cannot be completely covered, so that re-scanning is required, thereby causing additional radiation injury to the patient.

For example, in the scenario shown in FIG. 1, when a temporal bone region of an object to be scanned in FIG. 1 needs to be scanned, the location of a scanning table is usually adjusted by a person responsible for CT scanning based on experience in the prior art, and scanning parameters need to be manually adjusted. However, since the person responsible for scanning cannot know an actual scanning effect without actually performing the scanning, positioning can only be performed roughly, and whether second scanning is needed is confirmed according to a scanning result after the scanning.

In the scheme provided by the embodiment of the present disclosure, two light sources and two detectors may be, for example, arranged on a scanning support at an angle. For example, the first light source may be configured with a large field-of-view detector to achieve full-view scanning. The second light source may be configured with a small field-of-view detector to achieve detailed-view scanning.

In the embodiment of the present disclosure, the area of the detector corresponding to the full-view scanning may be at least twice the area of the detector corresponding to the detailed-view scanning. Therefore, a fixed reference phantom may be first imaged by dual-camera imaging apparatus to obtain dual-camera images of the phantom. The reference phantom may then be subjected to CT scanning to obtain a CT image thereof. A relationship between a CT system coordinate system and a dual-camera imaging coordinate system may then be calibrated through surface feature points of a scanned CT image of the reference phantom thus obtained and dual-camera images corresponding thereto, and the relationship may be referred to as A_V2CT in the embodiment of the present disclosure.

Then, when an actual object to be scanned is scanned, two body surface images of a part to be scanned of the object to be scanned may be obtained, coordinates xv1, xv2, xv3, . . . of mark points such as auricles, orbits, and eyebrow peaks in the dual-camera coordinate system are determined according to the images, and a coordinate $x_v^{cntr}$ of a central point of a region to be scanned in the dual-camera coordinate system is further determined according to these coordinates. $x_v^{cntr}$ is converted to a CT system coordinate system $x_{CT}^{cntr}$ according to A_V2CT calibrated above. The scanning table may be controlled to move to a location indicated thereby according to coordinates of $x_{CT}^{cntr}$, so that the center of a target scanning region is located at the center of a CT scanning region. In the embodiment of the present disclosure, the CT scanning table may move in three degrees of freedom: up-down, left-right, and front-back.

Therefore, in the embodiment of the present disclosure, the scanning table may be driven to move to a first location in three directions through coordinate information calculated according to the dual-camera images, thereby achieving automatic positioning.

Furthermore, in the embodiment of the present disclosure, the above auricles, orbits, eyebrow peaks, and other mark points may be located in the dual-camera images through a neural network model. For example, a plurality of sets of body surface images may be collected by using a dual-camera imaging system, and the auricles, orbits, eyebrow peaks, and other mark points of each set of body surface images may be labeled to obtain a first training data set. The neural network model is trained by using the first training data set to obtain a first neural network model for locating the auricles, orbits, eyebrow peaks, and other mark points. Therefore, in practical use, images obtained by a dual-camera image acquisition device may be input into the trained first neural network model to obtain locating information of the auricles, orbits, eyebrow peaks, and other mark points.

For example, in the embodiment of the present disclosure, it is possible to use, for example, a Yolo V4 neural network model as a neural network model for detecting the auricles, orbits, eyebrows, and other mark points and to obtain coordinates $x_i$, $x_j$ of a feature region and an image of a local region by inputting the dual-camera images into the neural network model.

Then, the detected local region may first be stretched to 64*64. The stretching ratios in rows and columns of an image may be a and b, respectively, and pixel coordinates $l_i$, $l_j$ of a mark point on the image of the local region are obtained by using a two-layer convolution network and a two-layer fully connected network. Location information of the mark point in the full figure is obtained according to $$x_i + \frac{l_i}{a}, x_j + \frac{l_j}{b}.$$

The coordinates of mark points in the CT system coordinate system may then be calculated by using the coordinates of the mark points paired according to dual-camera imaging, for example, a coordinate point of an eyebrow peak in an image obtained by camera 1 and a coordinate point in an image obtained by camera 2 to obtain coordinates of a plurality of mark points $x_{v1}$, $x_{v2}$, $x_{v3}$, .... A central location of the temporal bone region is determined according to a weighted average of the locations of a plurality of locating mark points. Thus, the scanning table may be moved so that the central location is at the center of the CT detailed-view scanning region, thereby completing an automatic positioning operation.

After the positioning of the object to be scanned is completed as described above, a front-back direction projection image and a side-side direction projection image of the part to be scanned may be obtained through full-view scanning. Alternatively, the front-back direction projection at least includes from front to back direction projection and from back to front direction projection image, and the side-side direction projection at least includes from one side to another side direction projection, for example, from right to left direction projection, and from left to right direction projection. Locating information, scanning region information and exposure parameter information of a detailed-view region of an image to be scanned are calculated according to the projection images by using, for example, the trained neural network model. Then, the scanning table may be driven to move in three directions according to the calculated locating information. Thus, the above object to be scanned which has been positioned may be secondarily adjusted to a location for detailed-view scanning, and a scanning operation may then be performed by using the calculated scanning region information such as temporal bone region density information and exposure information.

In the embodiment of the present disclosure, historical head CT data may be used to generate projection images in both back-front and left-right directions, and to label a scanning region of a temporal bone region in the projection images thus generated. It is also possible to use both back-front and left-right projection images of a historical head of cone-beam CT with similar parameters and to label the scanning region of the temporal bone region therein. It is also possible to use a specimen CT projection image and to label the scanning region of the temporal bone region therein. A radiation dose for CT scanning has been obtained by using a dose phantom to perform CT scanning with different exposure parameter combinations. It is also possible to use a head phantom to perform CT scanning with different exposure parameter combinations and to perform quality evaluation on the obtained CT scanning image. Optimized exposure parameters may thus be determined according to the image quality and the radiation dose.

Furthermore, in the embodiment of the present disclosure, it is also possible to use one or more of the above data to constitute a second training data set, and to use the above second training data set to train a neural network model, so that a projection image may be input into the trained neural network model in use to determine the scanning region of the temporal bone region, scanning parameters, etc.

For example, a Yolo V4 neural network model may be used to detect a scanning region and a label region in the obtained back-front projection image to obtain central coordinates $x_j$, $x_{k1}$ of a feature region. Also, the neural network model is used to detect a scanning region and a label region in the left-right projection image to obtain central coordinates $x_i$, $x_{k2}$ of the feature region. Therefore, the position of the scanning table is finely adjusted according to $$x_i, x_j, \frac{x_{k1} + x_{k2}}{2}.$$

That is, $$x_i, x_j, \frac{x_{k1} + x_{k2}}{2}$$

are adjusted to the center of the detailed-view scanning region. Furthermore, the scanning may be controlled by using the calculated acquisition region information, exposure parameter information and the like as scanning control parameters.

The exposure parameters calculated above for actual scanning may include light source tube voltage (kV), tube current (mA), exposure time (s), etc. And the radiation dose phantom may have different sizes to respectively calculate physical parameters of absorption of human heads of different age groups, such as newborns, children and adults to X-ray radiation emitted by CT scanning.

Furthermore, the image quality evaluation for a head phantom may include subjective evaluation and objective evaluation, and the total evaluation result is calculated according to accumulated scores. For example, the subjective evaluation may be performed by at least two doctors making blind scoring in image definition, structure sharpness, degree of artifact, etc. with a maximum score of not less than 3 respectively, and the scores are accumulated to obtain a subjective score.

Furthermore, the objective evaluation may be performed by calculating an objective index. A mean value and a mean square error of each index such as a signal-to-noise ratio and a contrast-to-noise ratio for measured values of all images are calculated. The image is assigned with a score according to the mean value and the mean square error: setting an image score of an index value within the range of mean value±0.5×standard deviation as A (A≥3), wherein the score is increased by 1 as the increase of 0.5 times of standard deviation, and is decreased by 1 as the decrease of 0.5 times of standard deviation. The objective score is obtained by adding multiple index scores. Therefore, a total image quality score in the embodiment of the present disclosure may be the sum of the subjective score and the objective score.

Furthermore, in the embodiment of the present disclosure, a balance factor may also be used to determine an optimal parameter combination according to the following formula: image quality−balance factor of radiation dose=total image quality score÷radiation dose.

Therefore, CT scanning result data may be obtained in the above manner, and then a CT image may be generated according to the CT scanning result. For example, in the embodiment of the present disclosure, the CT image may be generated by using a detailed-view high-resolution image obtained in the above manner and a full-view conventional-resolution image obtained using a conventional means.

For example, a local target region of detailed-view scanning may be represented by ROI in the embodiment of the present disclosure. For example, the high-resolution CT scanning data obtained in the above manner is: $g^{HR-ROI}=H^{HR-ROI}\mu^{HR-ROI}$, where $\mu^{HR-ROI}$ is the local high-resolution linear attenuation coefficient distribution, and $g^{HR-ROI}$ is projection data corresponding to a high-resolution detector. In the embodiment of the present disclosure, the projection data may be data after subtracting background, dividing by air, and taking negative logarithm. $H^{HR-ROI}$ is a system matrix at a high resolution. The conventional-resolution CT scanning data obtained using a conventional scanning means is: $g^{NR}=H^{NR}\mu^{NR}$, where $\mu^{NR}$ is a global conventional-resolution linear attenuation coefficient distribution, and $g^{NR}$ is projection data corresponding to a conventional-resolution detector. In the embodiment of the present disclosure, the projection data may be data after subtracting background, dividing by air, and taking negative logarithm. $H^{NR}$ is a system matrix at a global conventional resolution.

In the embodiment of the present disclosure, an attenuated image of a high-resolution field may be reconstructed in two manners.

1) High-resolution data $\bar{g}^{HR-ROI}$ beyond a temporal bone region is obtained by high-resolution interpolation on $g^{NR}$, and is combined with $g^{HR-ROI}$ to obtain $g^{HR}$, and an image in a detailed-view field is reconstructed by using $g^{HR}$ according to a cone-beam CT analytical reconstruction method in the field. Various methods known in the art may thus be used to reconstruct a conventional-resolution full-view image.

2) Conventional-resolution grid pixels beyond a high-resolution ROI are defined as $\bar{\mu}^{NR}$, so that a hybrid-resolution image to be reconstructed is μ:

$$\mu = \begin{cases} \bar{\mu}^{NR}, & ROI \text{ outside} \\ \mu^{HR-ROI}, & ROI \text{ inside} \end{cases}.$$

A system matrix under a hybrid-resolution reconstruction grid corresponding to data acquired by a high-resolution detector is defined as $H^{HR-hybrid}$, and a system matrix under a hybrid-resolution reconstruction grid corresponding to data acquired by a conventional-resolution detector is defined as $H^{NR-hybrid}$, thereby deriving:

$$g^{HR-ROI}=HH^{R-hybrid}\mu$$

$$g^{NR}=H^{NR-hybrid}\mu$$

In combination with a noise model, an iterative algorithm based on posterior probability optimization may be obtained to reconstruct the hybrid-resolution image:

$$\mu = \underset{\mu}{\operatorname{argmin}}\, L(g^{HR-ROI};\mu) + \alpha L(g^{NR};\mu) + \beta R(\mu)$$

where $L(g^{HR-ROI};\mu)$ and $L(g^{NR};\mu)$ are likelihood functions, $R(\mu)$ is a regularization term, $\alpha$ and $\beta$ are adjustable hyper-parameters, and argmin is an operation for solving a minimum function parameter value $\mu$. The optimization process of this objective function may be completed by using an iterative method to solve the optimization problem.

For example, in the embodiment of the present disclosure, the CT image may be reconstructed in the following manners. First, $g^{NR}$ and $g^{HR-ROI}$ are denoised. The denoised conventional-resolution data $g^{NR}$ may then be used to obtain high-sample-rate data corresponding to regions beyond a ROI by bilinear interpolation for each layer of data. The interpolated data beyond the ROI and the denoised detailed-view data $g^{HR-ROI}$ are merged and multiplied by a weighting function q, and the detailed-view region data is kept unchanged, but gradually and smoothly falls to zero to reduce the influence of the interpolated data. Data thus obtained may be denoted as $\hat{g}^{HR}$. The data is weighted and filtered by an FDK reconstruction method. Weighted back projection is performed on the filtered data after the detailed-view region is intercepted. The back projection operation may use various back projection algorithms commonly used in the art, and in the embodiment of the present disclosure, only the intercepted detailed-view region of the data and the image may be involved.

Therefore, in the CT scanning scheme provided by the embodiment of the present disclosure, according to dual-camera images of a part to be scanned, a first coordinate of a mark point of the part to be scanned in a dual-camera imaging coordinate system is determined. The first coordinate is converted into a second coordinate in a CT coordinate system according to coordinate system transformation parameters. Thus, first locating information is generated according to the second coordinate to drive a scanning table to move to a first location designated by the first locating information. Then, projection images of the part to be scanned are obtained. Second locating information and scanning information of the part to be scanned are determined according to the projection images. The scanning table is driven to move to a second location designated by the second locating information according to the second locating information and CT scanning is performed according to the scanning information. Thus, it is possible to determine a first location of a full-view scanning region according to the dual-camera images and a second location of a detailed-view scanning region according to the projection images as well as parameters for detailed-view scanning, whereby a target with a fine structure can be automatically positioned and accurately imaged through combining a full-view and detailed-view scan, and the defects of manual positioning and poor scanning effects in the prior art can be eliminated.

The above embodiment is illustration of the technical principles and exemplary application frameworks of the embodiment of the present disclosure, and the specific technical solutions of the embodiment of the present disclosure are further described in detail through multiple embodiments.

Embodiment 2

Figure 2:
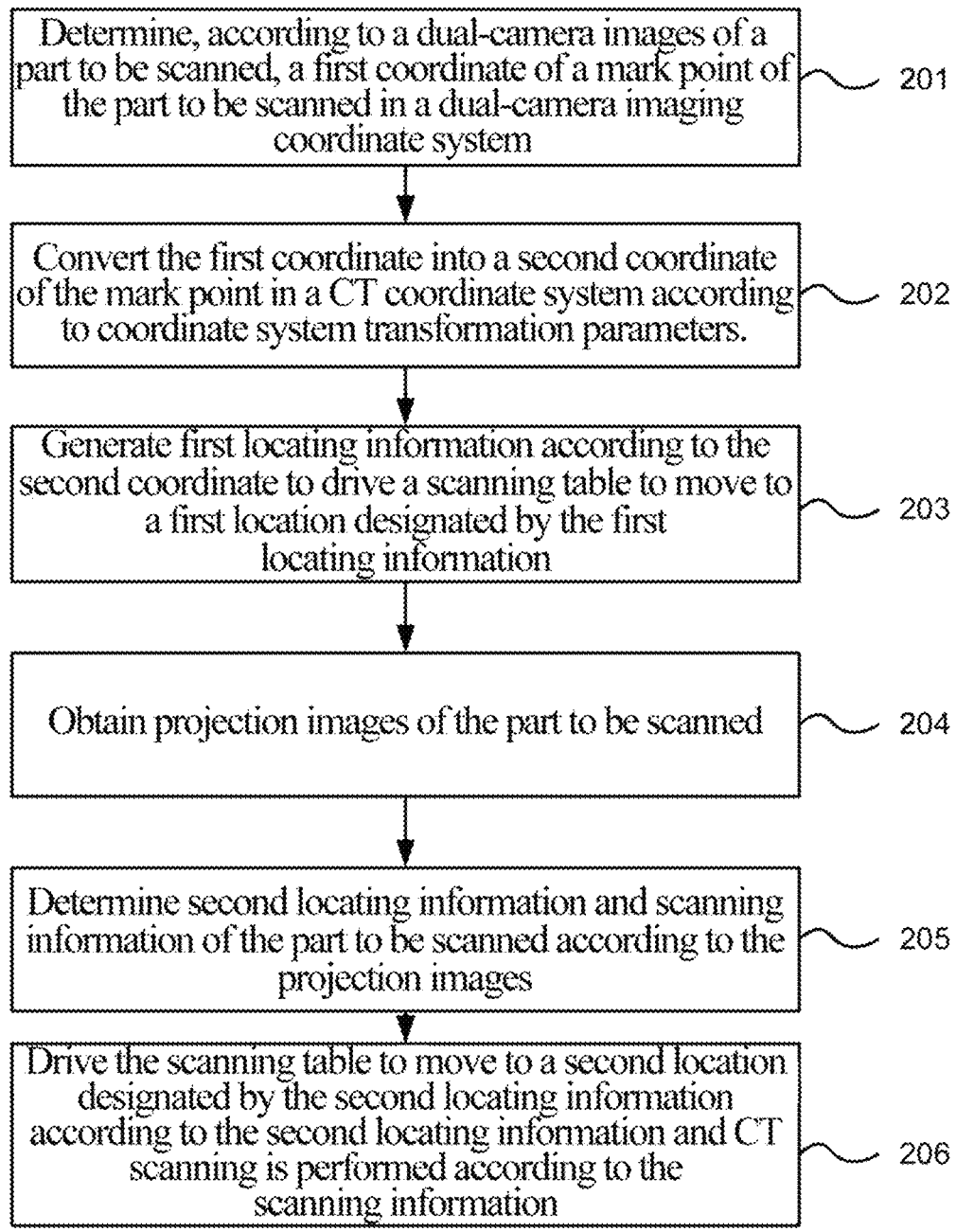
FIG. 2 is a flowchart of one embodiment of a CT scanning method according to the present disclosure.

FIG. 2 is a flowchart of one embodiment of a CT scanning method according to the present disclosure. As shown in FIG. 2, the CT scanning method may include the following steps.

At S201, according to a dual-camera images of a part to be scanned, a first coordinate of a mark point of the part to be scanned in a dual-camera imaging coordinate system is determined.

In the embodiment of the present disclosure, dual-camera images of a part to be scanned may be obtained by a dual-camera imaging apparatus. In step S201, coordinates of mark points, such as auricles, orbits and eyebrow peaks, of a part to be imaged by a dual-camera imaging system may be obtained according to such dual-camera images. For example, the above auricles, orbits, eyebrow peaks, and other mark points may be located in the dual-camera images through a neural network model. For example, a plurality of sets of body surface images may be collected by using a dual-camera imaging system, and the auricles, orbits, eyebrow peaks, and other mark points of each set of body surface images may be labeled to obtain a first training data set. The neural network model is trained by using the first training data set to obtain a first neural network model for locating the auricles, orbits, eyebrow peaks, and other mark points. Therefore, in practical use, images obtained by a dual-camera imaging device may be input into the trained first neural network model to obtain locating information of the auricles, orbits, eyebrow peaks, and other mark points.

At S202, the first coordinate is converted into a second coordinate of the mark point in a CT coordinate system according to coordinate system transformation parameters.

After the first coordinate is obtained in step S201, the first coordinate may be transformed into a second coordinate in a CT coordinate system according to coordinate system transformation parameters. For example, the transformation in step S202 may be performed by using a pre-calculated transformation parameter. For example, a fixed reference phantom may be first imaged by a dual-camera imaging apparatus to obtain images of the phantom. The reference phantom may then be subjected to CT scanning to obtain a CT image thereof. A relationship between a CT system coordinate system and a dual-camera coordinate system may then be calibrated through surface feature points of a scanned CT image of the reference phantom thus obtained and dual-camera images corresponding thereto.

At S203, first locating information is generated according to the second coordinate to drive a scanning table to move to a first location designated by the first locating information.

In step S203, it is possible to control, for example, a scanning table to be moved to a location designated by the first locating information according to the coordinates transformed into the CT coordinate system in step S202. Thus, an automatic positioning operation is realized.

At S204, projection images of the part to be scanned are obtained.

At S205, second locating information and scanning information of the part to be scanned are determined according to the projection images.

At S206, the scanning table is driven to move to a second location designated by the second locating information according to the second locating information and CT scanning is performed according to the scanning information.

After the positioning of the object to be scanned is completed in step S203, a front-back direction projection image and a side-side direction projection image of the part to be scanned may be obtained through, for example, full-view scanning in step S204. In step S205, locating information, scanning region information and exposure parameter information of a detailed-view region of an image to be scanned may be calculated according to the projection images by using, for example, the trained neural network model. Then, the scanning table may be driven to move in three directions according to the calculated locating information in step S206. Thus, the object to be scanned which has been positioned in step S203 may be secondarily adjusted in step S206 to a location for detailed-view scanning, and a scanning operation may then be performed by using the calculated scanning region information such as temporal bone region density information and exposure information.

Furthermore, in the embodiment of the present disclosure, in order to determine the second locating information and the scanning information according to the projection images in step S205, historical head CT data may be used to generate projection images in both back-front and left-right directions, and to label a scanning region of a temporal bone region in the projection images thus generated. It is also possible to use both back-front and left-right projection images of a historical head of cone-beam CT with similar parameters and to label the scanning region of the temporal bone region therein. It is also possible to use a specimen CT projection image and to label the scanning region of the temporal bone region therein. A radiation dose for CT scanning has been obtained by using a dose phantom to perform CT scanning with different exposure parameter combinations. It is also possible to use a head phantom to perform CT scanning with different exposure parameter combinations and to perform quality evaluation on the obtained CT scanning image. Optimized exposure parameters may thus be determined according to the image quality and the radiation dose.

In the embodiment of the present disclosure, it is also possible to use one or more of the above data to constitute a second training data set, and to use the above second training data set to train a neural network model, so that a projection image may be input into the trained neural network model in use to determine the scanning region of the temporal bone region, scanning parameters, etc.

For example, a Yolo V4 neural network model may be used to detect a scanning region and a label region in the obtained back-front projection image to obtain central coordinates $x_j$, $x_{k1}$ of a feature region. Also, the neural network model is used to detect a scanning region and a label region in the left-right projection image to obtain central coordinates $x_i$, $x_{k2}$ of the feature region. Therefore, the position of the scanning table is finely adjusted according to $$x_i, x_j, \frac{x_{k1} + x_{k2}}{2}.$$

That is, $$x_i, x_j, \frac{x_{k1} + x_{k2}}{2}$$

are adjusted to the center of the detailed-view scanning region. Furthermore, the scanning may be controlled by using the calculated acquisition region information, exposure parameter information and the like as scanning control parameters.

The exposure parameters calculated above for actual scanning may include light source tube voltage (kV), tube current (mA), exposure time (s), etc. And the radiation dose phantom may have different sizes to respectively calculate physical parameters of absorption of human heads of different age groups, such as newborns, children and adults to X-ray radiation emitted by CT scanning.

Furthermore, the image quality evaluation for a head phantom may include subjective evaluation and objective evaluation, and the total evaluation result is calculated according to accumulated scores. For example, the subjective evaluation may be performed by at least two doctors making blind scoring in image definition, structure sharpness, degree of artifact, etc. with a maximum score of not less than 3 respectively, and the scores are accumulated to obtain a subjective score.

Furthermore, the objective evaluation may be performed by calculating an objective index. A mean value and a mean square error of each index such as a signal-to-noise ratio and a contrast-to-noise ratio for measured values of all images are calculated. The image is assigned with a score according to the mean value and the mean square error: setting an image score of an index value within the range of mean value±0.5×standard deviation as A (A≥3), wherein the score is increased by 1 as the increase of 0.5 times of standard deviation, and is decreased by 1 as the decrease of 0.5 times of standard deviation. The objective score is obtained by adding multiple index scores. Therefore, a total image quality score in the embodiment of the present disclosure may be the sum of the subjective score and the objective score.

Furthermore, in the embodiment of the present disclosure, a balance factor may also be used to determine an optimal parameter combination according to the following formula: image quality–balance factor of radiation dose=total image quality score÷radiation dose.

Therefore, the second locating information and information such as the scanning region information and exposure parameters may be determined in step S205 in the manner described above, and then a CT image may be generated according to the CT scanning result. For example, in the embodiment of the present disclosure, the CT image may be generated based on the scanning data obtained in step S206 and a conventional-resolution image obtained using a conventional means.

For example, a local target region of detailed-view scanning may be represented by ROI in the embodiment of the present disclosure. For example, the detailed-view high-resolution CT scanning data obtained in the above manner is: $g^{HR-ROI} = H^{HR-ROI} \mu^{HR-ROI}$, where $\mu^{HR-ROI}$ is the local high-resolution linear attenuation coefficient distribution, and $g^{HR-ROI}$ is projection data corresponding to a high-resolution detector. In the embodiment of the present disclosure, the projection data may be data after subtracting background, dividing by air, and taking negative logarithm. $H^{HR-ROI}$ is a system matrix at a high resolution. The conventional-resolution CT scanning data obtained using a conventional scanning means is: $g^{NR} = H^{NR} \mu^{NR}$, where $\mu^{NR}$ is a global conventional-resolution linear attenuation coefficient distribution, and $g^{NR}$ is projection data corresponding to a conventional-resolution detector. In the embodiment of the present disclosure, the projection data may be data after subtracting background, dividing by air, and taking negative logarithm. $H^{NR}$ is a system matrix at a global conventional resolution.

In the embodiment of the present disclosure, an attenuated image of a high-resolution field may be reconstructed in two manners.

1) High-resolution data $\bar{g}^{HR-ROI}$ beyond a temporal bone region is obtained by high-resolution interpolation on $g^{NR}$, and is combined with $g^{HR-ROI}$ to obtain $g^{HR}$, and an image in a detailed-view field is reconstructed by using $g^{HR}$ according to a cone-beam CT analytical reconstruction method in the field. Various methods known in the art may thus be used to reconstruct a conventional-resolution full-view image.

2) Conventional-resolution grid pixels beyond a high-resolution ROI are defined as $\bar{\mu}^{NR}$, so that a hybrid-resolution image to be reconstructed is μ:

$$\mu = \begin{cases} \bar{\mu}^{NR}, & ROI \text{ outside} \\ \mu^{HR-ROI}, & ROI \text{ inside} \end{cases}.$$

A system matrix under a hybrid-resolution reconstruction grid corresponding to data acquired by a high-resolution detector is defined as $H^{HR-hybrid}$, and a system matrix under a hybrid-resolution reconstruction grid corresponding to data acquired by a conventional-resolution detector is defined as $H^{NR-hybrid}$, thereby deriving:

$$g^{HR-ROI} = H^{HR-hybrid} \mu$$

$$g^{NR} = H^{NR-hybrid} \mu$$

In combination with a noise model, an iterative algorithm based on posterior probability optimization may be obtained to reconstruct the hybrid-resolution image:

$$\mu = \underset{\mu}{\arg\min}\, L(g^{HR-ROI}; \mu) + \alpha L(g^{NR}; \mu) + \beta R(\mu)$$

where $L(g^{HR-ROI}; \mu)$ and $L(g^{NR}; \mu)$ are likelihood functions, $R(\mu)$ is a regularization term, $\alpha$ and $\beta$ are adjustable hyper-parameters, and argmin is an operation for solving a minimum function parameter value μ. The optimization process of this objective function may be completed by using an iterative method to solve the optimization problem.

For example, in the embodiment of the present disclosure, the CT image may be reconstructed in the following manners. First, $g^{NR}$ and $g^{HR\text{-}ROI}$ are denoised. The denoised conventional-resolution data $g^{NR}$ may then be used to obtain high-sample-rate data corresponding to regions beyond a ROI by bilinear interpolation for each layer of data. The interpolated data beyond the ROI and the denoised detailed-view data $g^{HR\text{-}ROI}$ are merged and multiplied by a weighting function q, and the detailed-view region data is kept unchanged, but gradually and smoothly falls to zero to reduce the influence of the interpolated data. Data thus obtained may be denoted as $ĝ^{HR}$. The data is weighted and filtered by an FDK reconstruction method [1]. Weighted back projection is performed on the filtered data after the detailed-view region is intercepted. The back projection operation may use various back projection algorithms commonly used in the art, and in the embodiment of the present disclosure, only the intercepted detailed-view region of the data and the image may be involved.

Therefore, in the CT scanning method provided by the embodiment of the present disclosure, according to dual-camera images of a part to be scanned, a first coordinate of a mark point of the part to be imaged in a dual-camera coordinate system is determined. The first coordinate is converted into a second coordinate in a CT coordinate system according to coordinate system transformation parameters. Thus, first locating information is generated according to the second coordinate to drive a scanning table to move to a first location designated by the first locating information. Then, projection images of the part to be scanned are obtained. Second locating information and scanning information of the part to be scanned are determined according to the projection images. The scanning table is driven to move to a second location designated by the second locating information according to the second locating information and CT scanning is performed according to the scanning information. Thus, it is possible to determine a first location of a full-view scanning region according to the dual-camera images and a second location of a detailed-view scanning region according to the projection images as well as parameters for detailed-view scanning, whereby a target with a fine structure can be automatically positioned and accurately imaged through combining a full-view and detailed-view scan, and the defects of manual positioning and poor scanning effects in the prior art can be eliminated.

Embodiment 3

Figure 3:
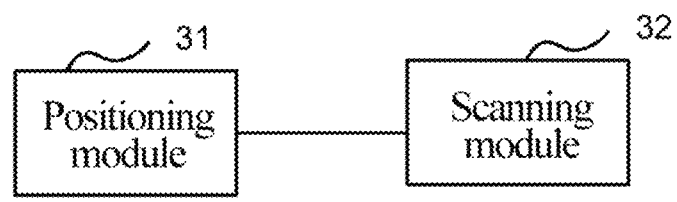
FIG. 3 is a schematic structure diagram of one embodiment of a CT scanning system according to the present disclosure.

FIG. 3 is a schematic structure diagram of one embodiment of a CT scanning system according to the present disclosure. The system may be used to perform the steps of the method as shown in FIG. 2. As shown in FIG. 3, the CT scanning system may include: a positioning module 31 and a scanning module 32.

The positioning module 31 is configured to determine, according to dual-camera images of a part to be scanned, a first coordinate of a mark point of the part to be imaged in a dual-camera coordinate system, convert the first coordinate into a second coordinate of the mark point in a CT coordinate system according to coordinate system transformation parameters, and generate first locating information according to the second coordinate to drive a scanning table to move to a first location designated by the first locating information.

In the embodiment of the present disclosure, images of a part to be scanned may be obtained by a dual-camera imaging apparatus. Coordinates of mark points, such as auricles, orbits and eyebrow peaks, of a part to be scanned of an object to be imaged in a dual-camera coordinate system may be obtained according to such dual-camera images. For example, the above auricles, orbits, eyebrow peaks, and other mark points may be located in the dual-camera images through a neural network model. For example, a plurality of sets of body surface images may be collected by using a dual-camera imaging system, and the auricles, orbits, eyebrow peaks, and other mark points of each set of body surface images may be labeled to obtain a first training data set. The neural network model is trained by using the first training data set to obtain a first neural network model for locating the auricles, orbits, eyebrow peaks, and other mark points. Therefore, in practical use, images obtained by a dual-camera imaging device may be input into the trained first neural network model to obtain locating information of the auricles, orbits, eyebrow peaks, and other mark points.

After the first coordinate is obtained, the first coordinate may be transformed into a second coordinate in a CT coordinate system according to coordinate system transformation parameters. For example, the transformation in step S202 may be performed by using a pre-calculated transformation parameter. For example, a fixed reference phantom may be first imaged by a dual-camera imaging apparatus to obtain dual-camera images of the phantom. The reference phantom may then be subjected to CT scanning to obtain a CT image thereof. A relationship between a CT system coordinate system and a dual-camera coordinate system may then be calibrated through surface feature points of a scanned CT image of the reference phantom thus obtained and dual-camera images corresponding thereto.

It is possible to control, for example, a scanning table to be moved to a location designated by the first locating information according to the coordinates transformed into the CT coordinate system. Thus, an automatic positioning operation is realized.

The scanning module 32 is configured to obtain projection images of the part to be scanned, wherein the projection images includes a front-back direction projection image and a side-side direction projection image for the part to be scanned; determine second locating information and scanning information of the part to be scanned according to the projection images, wherein the scanning information includes scanning region information and exposure parameter information; and drive the scanning table to move to a second location designated by the second locating information according to the second locating information and perform CT scanning according to the scanning information.

After the positioning of the object to be scanned is completed, a front-back direction projection image and a side-side direction projection image of the part to be scanned may be obtained through, for example, full-view scanning. Locating information, scanning region information and exposure parameter information of a detailed-view region of an image to be scanned may be calculated according to the projection images by using, for example, the trained neural network model. Then, the scanning table may be driven to move in three directions according to the calculated locating information. Thus, the object to be scanned which has been positioned may be secondarily adjusted to a location for detailed-view scanning, and a scanning operation may then be performed by using the calculated scanning region information such as temporal bone region density information and exposure information.

Furthermore, in the embodiment of the present disclosure, in order to determine the second locating information and the scanning information according to the projection images, historical head CT data may be used to generate projection images in both back-front and left-right directions, and to label a scanning region of a temporal bone region in the projection images thus generated. It is also possible to use both back-front and left-right projection images of a historical head of cone-beam CT with similar parameters and to label the scanning region of the temporal bone region therein. It is also possible to use a specimen CT projection image and to label the scanning region of the temporal bone region therein. A radiation dose for CT scanning has been obtained by using a dose phantom to perform CT scanning with different exposure parameter combinations. It is also possible to use a head phantom to perform CT scanning with different exposure parameter combinations and to perform quality evaluation on the obtained CT scanning image. Optimized exposure parameters may thus be determined according to the image quality and the radiation dose.

In the embodiment of the present disclosure, it is also possible to use one or more of the above data to constitute a second training data set, and to use the above second training data set to train a neural network model, so that a projection image may be input into the trained neural network model in use to determine the scanning region of the temporal bone region, scanning parameters, etc.

For example, a Yolo V4 neural network model may be used to detect a scanning region and a label region in the obtained back-front projection image to obtain central coordinates $x_j$, $x_{k1}$ of a feature region. Also, the neural network model is used to detect a scanning region and a label region in the left-right projection image to obtain central coordinates $x_i$, $x_{k2}$ of the feature region. Therefore, the position of the scanning table is finely adjusted according to $$x_i, x_j, \frac{x_{k1} + x_{k2}}{2}.$$

That is, $$x_i, x_j, \frac{x_{k1} + x_{k2}}{2}$$

are adjusted to the center of the detailed-view scanning region. Furthermore, the scanning may be controlled by using the calculated acquisition region information, exposure parameter information and the like as scanning control parameters.

The exposure parameters calculated above for actual scanning may include light source tube voltage (kV), tube current (mA), exposure time (s), etc. And the radiation dose phantom may have different sizes to respectively calculate physical parameters of absorption of human heads of different age groups, such as newborns, children and adults to X-ray radiation emitted by CT scanning.

Furthermore, the image quality evaluation for a head phantom may include subjective evaluation and objective evaluation, and the total evaluation result is calculated according to accumulated scores. For example, the subjective evaluation may be performed by at least two doctors making blind scoring in image definition, structure sharpness, degree of artifact, etc. with a maximum score of not less than 3 respectively, and the scores are accumulated to obtain a subjective score.

Furthermore, the objective evaluation may be performed by calculating an objective index. A mean value and a mean square error of each index such as a signal-to-noise ratio and a contrast-to-noise ratio for measured values of all images are calculated. The image is assigned with a score according to the mean value and the mean square error: setting an image score of an index value within the range of mean value±0.5×standard deviation as A (A≥3), wherein the score is increased by 1 as the increase of 0.5 times of standard deviation, and is decreased by 1 as the decrease of 0.5 times of standard deviation. The objective score is obtained by adding multiple index scores. Therefore, a total image quality score in the embodiment of the present disclosure may be the sum of the subjective score and the objective score.

Furthermore, in the embodiment of the present disclosure, a balance factor may also be used to determine an optimal parameter combination according to the following formula: image quality−balance factor of radiation dose=total image quality score÷radiation dose.

Therefore, the second locating information and information such as the scanning region information and exposure parameters may be determined in step S205 in the manner described above, and then a CT image may be generated according to the CT scanning result. For example, in the embodiment of the present disclosure, the CT image may be generated based on the scanning data obtained in step S206 and a conventional-resolution image obtained using a conventional means.

For example, a local target region of detailed-view scanning may be represented by ROI in the embodiment of the present disclosure. For example, the high-resolution CT scanning data obtained in the above manner is: $g^{HR\text{-}ROI}=H^{HR\text{-}ROI}\mu^{HR\text{-}ROI}$, where $\mu^{HR\text{-}ROI}$ is the local high-resolution linear attenuation coefficient distribution, and $g^{HR\text{-}ROI}$ is projection data corresponding to a high-resolution detector. In the embodiment of the present disclosure, the projection data may be data after subtracting background, dividing by air, and taking negative logarithm. $H^{HR\text{-}ROI}$ is a system matrix at a high resolution. The conventional-resolution CT scanning data obtained using a conventional scanning means is: $g^{NR}=H^{NR}\mu^{NR}$, where $\mu^{NR}$ is a global conventional-resolution linear attenuation coefficient distribution, and $g^{NR}$ is projection data corresponding to a conventional-resolution detector. In the embodiment of the present disclosure, the projection data may be data after subtracting background, dividing by air, and taking negative logarithm. $H^{NR}$ is a system matrix at a global conventional resolution.

In the embodiment of the present disclosure, an attenuated image of a high-resolution field may be reconstructed in two manners.

1) High-resolution data $\bar{g}^{HR\text{-}ROI}$ beyond a temporal bone region is obtained by high-resolution interpolation on $g^{NR}$, and is combined with $g^{HR\text{-}ROI}$ to obtain $g^{HR}$, and an image in a detailed-view field is reconstructed by using $g^{HR}$ according to a cone-beam CT analytical reconstruction method in the field. Various methods known in the art may thus be used to reconstruct a conventional-resolution full-view image.

2) Conventional-resolution grid pixels beyond a high-resolution ROI are defined as $\bar{\mu}^{NR}$, so that a hybrid-resolution image to be reconstructed is μ:

$$\mu = \begin{cases} \bar{\mu}^{NR}, & ROI \text{ outside} \\ \mu^{HR\text{-}ROI}, & ROI \text{ inside} \end{cases}.$$

A system matrix under a hybrid-resolution reconstruction grid corresponding to data acquired by a high-resolution detector is defined as $H^{HR\text{-}hybrid}$, and a system matrix under a hybrid-resolution reconstruction grid corresponding to data acquired by a conventional-resolution detector is defined as $H^{NR\text{-}hybrid}$, thereby deriving:

$$g^{HR\text{-}ROI} = H^{HR\text{-}hybrid} \mu$$

$$g^{NR} = H^{NR\text{-}hybrid} \mu$$

In combination with a noise model, an iterative algorithm based on posterior probability optimization may be obtained to reconstruct the hybrid-resolution image:

$$\mu^* = \underset{\mu}{\operatorname{argmin}} L(g^{HR\text{-}ROI}; \mu) + \alpha L(g^{NR}; \mu) + \beta R(\mu)$$

where $L(g^{HR\text{-}ROI}; \mu)$ and $L(g^{NR}; \mu)$ are likelihood functions, $R(\mu)$ is a regularization term, $\alpha$ and $\beta$ are adjustable hyper-parameters, and argmin is an operation for solving a minimum function parameter value $\mu$. The optimization process of this objective function may be completed by using an iterative method to solve the optimization problem.

For example, in the embodiment of the present disclosure, the CT image may be reconstructed in the following manners. First, $g^{NR}$ and $g^{HR\text{-}ROI}$ are denoised. The denoised conventional-resolution data $g^{NR}$ may then be used to obtain high-sample-rate data corresponding to regions beyond a ROI by bilinear interpolation for each layer of data. The interpolated data beyond the ROI and the denoised detailed-view data $g^{HR\text{-}ROI}$ are merged and multiplied by a weighting function q, and the detailed-view region data is kept unchanged, but gradually and smoothly falls to zero to reduce the influence of the interpolated data. Data thus obtained may be denoted as $\hat{g}^{HR}$. The data is weighted and filtered by an FDK reconstruction method [1]. Weighted back projection is performed on the filtered data after the detailed-view region is intercepted. The back projection operation may use various back projection algorithms commonly used in the art, and in the embodiment of the present disclosure, only the intercepted detailed-view region of the data and the image may be involved.

Therefore, in the CT scanning system provided by the embodiment of the present disclosure, according to dual-camera images of a part to be scanned, a first coordinate of a mark point of the part to be imaged in a dual-camera coordinate system is determined by using a positioning module. The first coordinate is converted into a second coordinate in a CT coordinate system according to coordinate system transformation parameters. Thus, first locating information is generated according to the second coordinate to drive a scanning table to move to a first location designated by the first locating information. Projection images of the part to be scanned are obtained by using a scanning module. Second locating information and scanning information of the part to be scanned are determined according to the projection images. The scanning table is driven to move to a second location designated by the second locating information according to the second locating information and CT scanning is performed according to the scanning information. Thus, it is possible to determine a first location of a full-view scanning region according to the dual-camera images and a second location of a detailed-view scanning region according to the projection images as well as parameters for detailed-view scanning, whereby a target with a fine structure can be automatically positioned and accurately imaged through combining a full-view and detailed-view scan, and the defects of manual positioning and poor scanning effects in the prior art can be eliminated.

Embodiment 4

Figure 4:
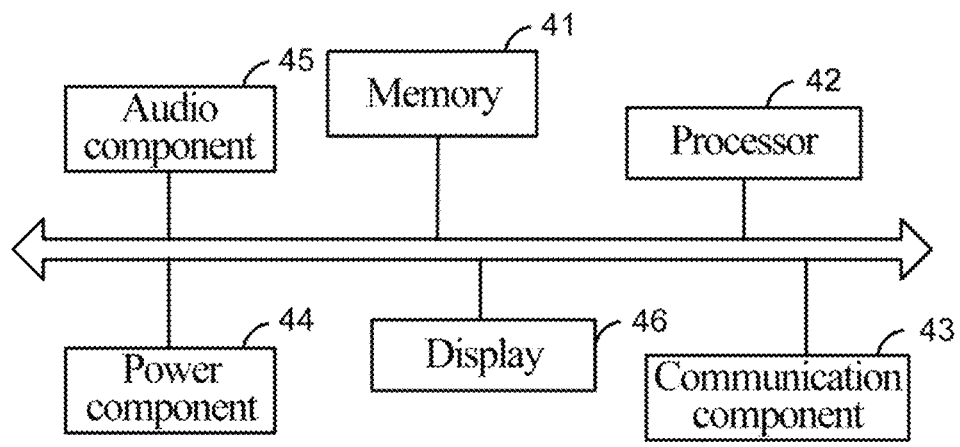
FIG. 4 is a schematic structure diagram of an embodiment of an electronic device according to the present disclosure.

The above describes the internal functions and structure of a CT scanning system, which may be implemented as an electronic device. FIG. 4 is a schematic structure diagram of an embodiment of an electronic device according to the present disclosure. As shown in FIG. 4, the electronic device includes a memory 41 and a processor 42.

The memory 41 is configured to store a program. In addition to storing the above program, the memory 41 may also be configured to store various other data to support operations on the electronic device. Examples of such data include instructions for any application or method operating on the electronic device, contact data, phonebook data, messages, pictures, videos, etc.

The memory 41 may be implemented by any type of volatile or non-volatile memory device or combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, and a magnetic or optical disk.

The processor 42 is not limited to a central processing unit (CPU), but may be a processing chip such as a graphics processing unit (GPU), a field programmable gate array (FPGA), an embedded neural network processing unit (NPU), or an artificial intelligence (AI) chip. The processor 42 is coupled to the memory 41, and executes the program stored in the memory 41. The program, when executed, performs the CT scanning method of Embodiment 2.

Further, as shown in FIG. 4, the electronic device may further include: a communication component 43, a power component 44, an audio component 45, a display 46, and other components. Only part of the components is shown schematically in FIG. 4. This does not mean that the electronic device includes only the components shown in FIG. 4.

The communication component 43 is configured to facilitate wired or wireless communication between the electronic device and other devices. The electronic device may access a wireless network based on a communication standard, such as Wi-Fi, 3G, 4G, or 5G, or a combination thereof. In one exemplary embodiment, the communication component 43 receives a broadcast signal or broadcast-related information from an external broadcast management system via a broadcast channel. In one exemplary embodiment, the communication component 43 also includes a near field communication (NFC) module to facilitate short-range communication. For example, the NFC module may be implemented based on a radio frequency identification (RFID) technology, an infrared data association (IrDA) technology, an ultra-wide band (UWB) technology, a Bluetooth (BT) technology, and other technologies.

The power component 44 supplies power to the various components of the electronic device. The power component 44 may include a power management system, one or more power supplies, and other components associated with generating, managing, and distributing power for the electronic device.

The audio component 45 is configured to output and/or input an audio signal. For example, the audio component 45 includes a microphone (MIC) configured to receive an external audio signal when the electronic device is in an operational mode, such as a call mode, a recording mode, and a speech recognition mode. The received audio signal may be further stored in the memory 41 or transmitted via the communication component 43. In some embodiments, the audio component 45 also includes a speaker for outputting the audio signal.

The display 46 includes a screen, which may include a liquid crystal display (LCD) and a touch panel (TP). If the screen includes a touch panel, the screen may be implemented as a touch screen to receive an input signal from a user. The TP includes one or more touch sensors to sense touches, slides, and gestures on the TP. The touch sensor may detect not only the boundary of a touch or slide action, but also the duration and pressure associated with the touch or slide operation.

Those ordinarily skilled in the art will appreciate that all or some of the steps to implement the method embodiments described above may be performed by hardware associated with program instructions. The aforementioned program may be stored in a computer-readable storage medium. The program, when executed, performs the steps including the various method embodiments described above. The aforementioned storage medium includes: various media capable of storing program codes, such as a ROM, a RAM, and a magnetic or optical disk.

Finally, it should be noted that the above various embodiments are merely illustration of the technical solutions of the present invention and are not restrictive. Although the present invention has been described in detail with reference to the aforementioned various embodiments, those ordinarily skilled in the art will appreciate that the technical solutions disclosed in the aforementioned various embodiments may still be modified, or some or all of the technical features thereof may be substituted equivalently. Such modifications or substitutions do not depart the corresponding technical solutions from the scope of the technical solutions in the various embodiments of the present invention in nature.

What is claimed is:

1. A CT scanning method, comprising:
    determining, according to dual-camera images of a part to be scanned, a first coordinate of a mark point of the part to be imaged in a dual-camera coordinate system;
    converting the first coordinate into a second coordinate of the mark point in a CT coordinate system according to coordinate system transformation parameters;
    generating first locating information according to the second coordinate to drive a scanning table to move to a first location designated by the first locating information;
    obtaining projection images of the part to be scanned, wherein the projection images comprises a front-back direction projection image and a side-side direction projection image for the part to be scanned;
    determining second locating information and scanning information of the part to be scanned according to the projection images, wherein the scanning information comprises scanning region information and exposure parameter information; and
    driving the scanning table to move to a second location designated by the second locating information according to the second locating information and performing CT scanning according to the scanning information.

2. The CT scanning method according to claim 1, further comprising:
    obtaining images of the part to be scanned through a dual-camera imaging device.

3. The CT scanning method according to claim 1, further comprising:
    scanning a reference phantom to obtain a CT image of the reference phantom;
    obtaining images of the reference phantom through a dual-camera imaging device; and
    determining coordinate system transformation parameters of the CT coordinate system and the dual-camera coordinate system according to coordinates of surface feature points in the CT image of the reference phantom and coordinates in the corresponding dual-camera images.

4. The CT scanning method according to claim 1, further comprising:
    collecting a plurality of sets of body surface images through a dual-camera imaging device;
    labeling coordinates of mark points in the plurality of sets of body surface images to form a first training data set; and
    training a neural network model by using the first training data set to obtain a first neural network model for locating the mark points; wherein,
    the determining, according to dual-camera images of a part to be scanned, a first coordinate of a mark point of the part to be imaged in a dual-camera coordinate system comprises:
    inputting the dual-camera images of the part to be scanned into the first neural network model to obtain the first coordinate of the mark point of the part to be scanned in the dual-camera coordinate system.

5. The CT scanning method according to claim 1, further comprising:
    obtaining a plurality of labeled projection images, wherein the labeled projection images comprise one or more of historical CT projection images, cone-beam CT projection images with similar parameters, and specimen CT projection images, and are labeled with scanning region information;
    obtaining a radiation dose for CT scanning using a dose phantom and different exposure parameter combinations;
    obtaining an image quality evaluation for CT scanning using a head phantom with different exposure parameter combinations;
    determining exposure parameters according to the radiation dose and the image quality evaluation; and
    training a neural network model by using the scanning region information and the exposure parameters as a second training data set to obtain a second neural network model for determining scanning information, wherein
    the determining second locating information and scanning information of the part to be scanned according to the projection images comprises:
    calculating the projection images by using the second neural network model to determine the second locating information and the scanning information.

6. The CT scanning method according to claim 1, further comprising:
    obtaining full-view scanning projection data and detailed-view scanning projection data;
    calculating conventional-resolution data of a region beyond the part to be scanned according to the full-view scanning projection data; and
    calculating detailed-view image data based on a conventional resolution beyond the region and the detailed-view scanning projection data.

7. The CT scanning method according to claim 1, further comprising:
obtaining full-view scanning grid pixel data and detailed-view scanning grid pixel data;
respectively calculating full-view projection data of a region beyond the part to be scanned and detailed-view high-resolution projection data for the part to be scanned according to the full-view scanning grid pixel data and the detailed-view scanning grid pixel data; and
calculating CT scanning image data by using an iterative algorithm based on the full-view projection data and the detailed-view high-resolution projection data.

8. A CT scanning system, comprising: a positioning module and a scanning module; wherein,
the positioning module is configured to determine, according to dual-camera images of a part to be scanned, a first coordinate of a mark point of the part to be scanned in a dual-camera coordinate system, convert the first coordinate into a second coordinate of the mark point in a CT coordinate system according to coordinate system transformation parameters, and generate first locating information according to the second coordinate to drive a scanning table to move to a first location designated by the first locating information; and
the scanning module is configured to obtain projection images of the part to be scanned, wherein the projection images comprises a front-back direction projection image and a side-side direction projection image for the part to be scanned; determine second locating information and scanning information of the part to be scanned according to the projection images, wherein the scanning information comprises scanning region information and exposure parameter information; and drive the scanning table to move to a second location designated by the second locating information according to the second locating information and perform CT scanning according to the scanning information.

9. The CT scanning system according to claim 8, wherein the positioning module is further configured to:
scan a reference phantom to obtain a CT image of the reference phantom;
obtain images of the reference phantom through a dual-camera imaging device; and
determine coordinate system transformation parameters of the CT coordinate system and the dual-camera coordinate system according to coordinates of surface feature points in the CT image of the reference phantom and coordinates in the corresponding dual-camera images.

10. The CT scanning system according to claim 8, further comprising:
a training module, configured to collect a plurality of sets of body surface images through dual-camera imaging device, label coordinates of mark points in the plurality of sets of body surface images to form a first training data set, and train a neural network model by using the first training data set to obtain a first neural network model for locating the mark points; wherein,
the positioning module is further configured to input the dual-camera images of the part to be scanned into the first neural network model to obtain the first coordinate of the mark point of the part to be imaged in the dual-camera coordinate system.

11. An electronic device, comprising:
a memory, configured to store a program; and
a processor, configured to execute the program stored in the memory to perform the CT scanning method according to claim 1.

12. A computer-readable storage medium, storing a computer program executable by a processor, wherein the program, when executed by the processor, implements the CT scanning method according to claim 1.

13. An electronic device, comprising:
a memory, configured to store a program; and
a processor, configured to execute the program stored in the memory to perform the CT scanning method according to claim 2.

14. An electronic device, comprising:
a memory, configured to store a program; and
a processor, configured to execute the program stored in the memory to perform the CT scanning method according to claim 3.

15. An electronic device, comprising:
a memory, configured to store a program; and
a processor, configured to execute the program stored in the memory to perform the CT scanning method according to claim 4.

16. An electronic device, comprising:
a memory, configured to store a program; and
a processor, configured to execute the program stored in the memory to perform the CT scanning method according to claim 5.

17. A computer-readable storage medium, storing a computer program executable by a processor, wherein the program, when executed by the processor, implements the CT scanning method according to claim 2.

18. A computer-readable storage medium, storing a computer program executable by a processor, wherein the program, when executed by the processor, implements the CT scanning method according to claim 3.

19. A computer-readable storage medium, storing a computer program executable by a processor, wherein the program, when executed by the processor, implements the CT scanning method according to claim 4.

20. A computer-readable storage medium, storing a computer program executable by a processor, wherein the program, when executed by the processor, implements the CT scanning method according to claim 5.

* * * * *